(12) United States Patent
Hassard et al.

(10) Patent No.: US 7,413,642 B2
(45) Date of Patent: Aug. 19, 2008

(54) MATERIAL SEPARATION DEVICE

(75) Inventors: John Hassard, London (GB); Ed McKigney, London (GB)

(73) Assignee: Deltadot Limited, London (GB)

( * ) Notice: Subject to any disclaimer, the term of this patent is extended or adjusted under 35 U.S.C. 154(b) by 215 days.

(21) Appl. No.: 10/520,303

(22) PCT Filed: Jul. 8, 2003

(86) PCT No.: PCT/GB03/02926

§ 371 (c)(1),
(2), (4) Date: Apr. 29, 2005

(87) PCT Pub. No.: WO2004/005910

PCT Pub. Date: Jan. 15, 2004

(65) Prior Publication Data

US 2005/0258041 A1    Nov. 24, 2005

(30) Foreign Application Priority Data

Jul. 8, 2002    (GB) ................................ 0215779.0

(51) Int. Cl.
*G01N 27/447*    (2006.01)
*B01L 3/02*    (2006.01)
(52) U.S. Cl. ...................................... 204/451; 422/100
(58) Field of Classification Search ......... 204/400–405, 204/600–605; 422/99, 100
See application file for complete search history.

(56) References Cited

U.S. PATENT DOCUMENTS 6,508,273 B1 * 1/2003 Van Den Berg ............. 137/827
6,964,736 B2 * 11/2005 Quake et al. ................ 204/452
7,024,281 B1 * 4/2006 Unno .......................... 700/275
7,216,660 B2 * 5/2007 Troian et al. .................. 137/13

FOREIGN PATENT DOCUMENTS

| EP | 0 816 837 A | 1/1998 |
|---|---|---|
| WO | WO 99/61888 A | 2/1999 |
| WO | WO 99/24827 A | 5/1999 |
| WO | WO 00/77511 A | 12/2000 |
| WO | WO 02/48177 A | 6/2002 |

OTHER PUBLICATIONS

Search Report for GB 2001/15779.0 dated Jan. 15, 2003.
International Search Report for PCT/GB2003/02926 dated Sep. 29, 2003.

* cited by examiner

*Primary Examiner*—Alex Noguerola
(74) *Attorney, Agent, or Firm*—Ungaretti & Harris LLP

(57) ABSTRACT

A separating device for use in separating electrically charged components, e.g., by electrophoresis, comprises a channel branched at a branch point to provide a main feed channel (105) connected to at least two subsidiary channels (110, 115). In use, different components (120, 125, 130) show differential migration along the feed channel (105) so they can be separated into different subsidiary channels (110, 115) at the branch point. To support this separation, the separating device is provided with switchable voltage control means for controlling local voltages in a region of the branch point to provide potential differences of opposing polarity along the respective subsidiary channels (110, 115) such that a component to be separated (125) can be caused to migrate from the feed channel into a different subsidiary channel (115) from one or more other components.

11 Claims, 3 Drawing Sheets

MATERIAL SEPARATION DEVICE

CROSS-REFERENCE TO RELATED APPLICATIONS

This Application is a U.S. National filing under § 371 of International Application No. PCT/GB03/002926, with an international filing date of Jul. 8, 2003, now pending, claiming priority from Great Britain Application No. GB02/15779.0, with a filing date of Jul. 8, 2002, now pending, and herein incorporated by reference.

1. Technical Field

The present invention relates to a device and to a method for separating materials (e.g. biomolecules). It finds particular although not exclusive application in microchannel voltage switching, for instance for use in electrophoresis.

2. Background of the Invention

Electrophoresis is a technique known for use in the laboratory to separate charged entities such as molecules. For example, DNA fragments can be separated out in this way. If an electric current is applied to a sample carried in a microchannel, the sample can be caused to migrate along the microchannel. In doing so, different constituents will migrate at different speeds so that the sample will separate out into constituent molecular bands positioned at varying distances along the microchannel.

The invention is not limited to molecular separations using electrophoresis, and is equally applicable to the separation of molecules or other components which are flowing in some other way along a channel. In the preferred embodiment, however, we are typically interested in the separation of DNA fragments, RNA fragments and/or proteins, with the separation and/or analysis being carried out in real-time.

A branched microchannel is, as its name suggests, a channel which branches into more than one channel. As the constituent molecular bands of a sample migrate along the microchannel, any one band will reach the branch point at a particular time. By applying an appropriately directed and timed potential difference at the branch point, the band currently migrating past that branch point can be selectively switched to migrate into a side channel.

A problem arises with this known arrangement when there is a need to change the potential difference at the branch point relatively rapidly, for instance to switch the next constituent molecular band into a different channel. There is a risk that at least the tail end of the constituent molecular band which has just been switched into a side channel will start to migrate back to the branch point and may leave the side channel again. Alternatively, the leading edge of the following constituent molecular band may start to follow the previous band into the same side channel. These effects can lead to cross-contamination of the separated constituent molecular bands.

SUMMARY OF THE INVENTION

According to a first embodiment of the present invention, there is provided a separating device for separating components flowing along a channel, the device comprising a main channel branched at a branch point, connected to at least two subsidiary channels, and switchable voltage control means for controlling a voltage in the region of the branch point to provide potential differences of opposing polarity along subsidiary channels such that components to be separated are caused to flow from the main channel into a selected subsidiary channel.

For instance the voltage control means can be arranged to provide a short section along a first subsidiary channel which has a negative potential difference in a direction away from the branch point, and a short section along a second subsidiary channel which has a positive potential difference in a direction away from the branch point. Negatively charged components will be driven into the second subsidiary channel under these conditions and blocked from entering the first subsidiary channel.

Embodiments of the present invention can be used to provide fast switching between collection channels for components with little cross-talk and thus precise collection of a component.

In an arrangement as just described, extremely good separation can be achieved between constituent molecular bands. At the moment of switching to apply the negative potential difference to the short section of the first subsidiary channel, a clean separation will be achieved between negatively charged components either side of the end of the short section. Negatively charged components which are still travelling within the short section will be driven back again to the branch point while negatively charged components which have already travelled beyond the short section will continue along the subsidiary channel (or vice versa).

The separation device may be fabricated in different ways. For instance, it might be constructed using a channel structure microfabricated into a chip. Alternatively, it might be provided as a branched capillary structure. The fabrication technique is likely to affect the suitable dimensions of a device and thus terms such as "short section" and "in the region of the branch point" will mean slightly different things in different circumstances. Typically, where a branched microchannel has been fabricated on a chip, these terms indicate a physical distance of the order of a few millimetres. In the case of the branched capillary structure, these terms indicate a physical distance of the order of a few centimetres. However, it is expected that these distances will substantially reduce in the future, as the technology develops and it becomes commercially realistic to produce channels of sub-micrometre sizes. In current systems, switching typically takes place within milliseconds (depending on the speed of the components to be separated, and the resolution required). The components may, for example, be between 1 and 50 µm apart.

The switchable voltage control means may be adapted, on switching, to reverse the polarity of the potential differences along each of two subsidiary channels at a branch point so that any one subsidiary channel can be selected to be subject to a different polarity from every other subsidiary channel at that branch point. Such an arrangement supports the separation of charged components into different respective subsidiary channels where there are several subsidiary channels at one branch point. Only one subsidiary channel should show a different polarity at any one time, in order to collect a component into it, but the subsidiary channel selected for collection of each component can be rotated through several available options at one branch point.

The voltage control means may conveniently be provided with a timer for use in controlling voltage in accordance with measured migration behaviour along the feed channel of the components to be separated. As long as the migration behaviour of a component it is desired to collect is known, it becomes possible to use such a timer for automated collection.

Alternatively or additionally, the voltage control means may be provided with a detector for use in controlling voltage, the detector being adapted to detect migration behaviour along the feed channel of at least one component to be separated. The use of a detector allows real time behaviour of a component to be taken into account. For instance, fluctuations in migration behaviour due to temperature changes which could produce cross contamination in a timed system can be immediately responded to.

Different arrangements might be used for providing the voltage control in the region of a branch point. For instance, in a first arrangement the separating device might comprise a first voltage source, for connection to at least one subsidiary channel to produce a potential difference along the feed channel and said at least one subsidiary channel, and a second voltage source for use by the voltage control means in the region of one or more branch points.

In a second arrangement, the separating device might comprise a voltage source for connection to all the subsidiary channels at the same time to produce a potential difference along the feed channel and each subsidiary channel, the voltage control means comprising means for short circuiting a point along the feed channel to a point along at least one of the subsidiary channels, in the region of the branch point for that subsidiary channel. This second arrangement is particularly advantageous because it means it is not necessary to switch a high voltage in order to change a subsidiary channel for collection of a component. This arises because the voltage source which is connected to produce a potential difference along the feed channel and at least one subsidiary channel is usually a high voltage source, designed to develop relatively quick differential migration of the components along the feed channel for collection into a subsidiary channel. By using the short circuiting arrangement described, only lower voltages need be switched to achieve the change in local conditions at a branch point which determine the direction taken by a component currently in the region of the branch point.

In a third arrangement, a separating device comprises a voltage source for connection to at least one subsidiary channel to produce a potential difference along the feed channel and said at least one subsidiary channel, wherein the voltage control means comprises a diode chain connected between the voltage source and earth, at least one subsidiary channel at a branch point being switchably connected to at least two alternative points in the diode chain so as to provide first and second configurations, the potential difference along the subsidiary channel in the region of the branch point in the first configuration having opposite polarity to that potential difference in the second configuration.

According to a second embodiment of the present invention, there is provided a method of separating an electrically charged component from a mixture, by differential flow along a branched channel structure, the method comprising the steps of:

(i) applying a force to the mixture so as to move the mixture along a main channel of a channel structure to a branch point connecting the main channel to at least two branch channels; and (ii) applying an electrical potential difference to a portion of each branch channel in the region of the branch point, wherein the electrical potential difference applied to a selected branch channel presents a polarity at the branch point which is different from the polarity presented at the branch point by an electrical potential difference applied to another branch channel at the said point.

The method may further comprise reversing the polarity presented by the electrical potential difference applied to the selected branch channel, and reversing the polarity presented by the electrical potential difference applied to one other branch channel at the branch point, so as to change the selected branch channel from a first to a second branch channel.

BRIEF DESCRIPTION OF THE DRAWINGS

A system for selecting the path of material flowing in an electrophoresis channel will now be described as an embodiment of the present invention, by way of example only, with reference to the accompanying figures in which.

DETAILED DESCRIPTION OF THE INVENTION

Figure 1:
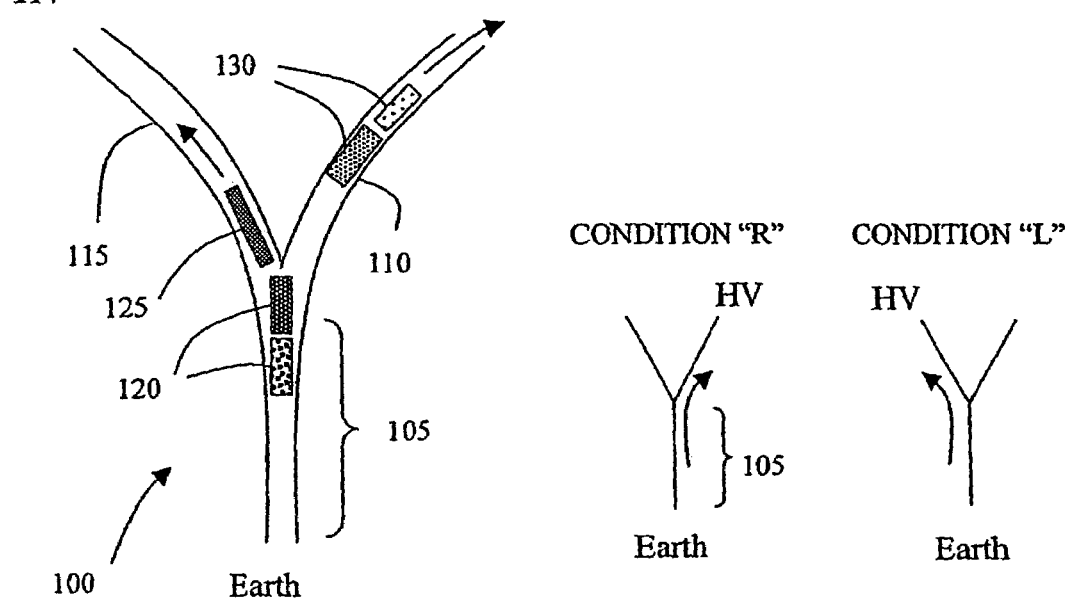
FIG. 1 shows schematically a branched microchannel for use in electrophoresis.

In electrophoresis, charged particles such as biomolecules move through a medium along a channel under the influence of an applied electric field. The channel can for instance be microfabricated on a chip, or might be a branched capillary tube. A voltage difference is applied between the ends of the channel. Charged particles inserted into the channel at one end (determined by the direction of the voltage difference and the effective charge of the particles) will move to the other end of the channel under the influence of the electric field. Particles having different characteristics move along the channel at different rates and thus mixed particles will separate into different groups as they move along the channel. It is useful to be able to collect one or more separated groups of particles and this can be accomplished by using a channel with multiple branches and by switching the flow of particles among the different branches in a timed fashion. One possible configuration of branched channel is illustrated in FIG. 1. Embodiments of the present invention can however be applied to any configuration and number of branched channels.

Referring to FIG. 1, a branched microchannel 100 for use in electrophoresis may comprise a generally "Y" shaped channel construction with means for applying a potential difference along it (not shown). A stem portion 105 is earthed at one end. At the other end, it branches into two side channels 110, 115 and a voltage ("HV") can be applied at the end of either side channel, or both side channels, to produce a potential difference along the length of the microchannel 100. Typically, the channel defined by the stem portion 105 may be about 50 μm wide and 200 μm deep. But channels of far smaller dimensions can be expected in the future, as the technology develops. The branch lines 110, 115 preferably have a combined cross sectional area which is approximately equal to that of the stem portion 105.

Although the point of the bifurcation is shown as being sharp in FIG. 1, it need not necessarily be so in a practical embodiment. In certain circumstances, it may be desirable for the bifurcation to be to a certain extent rounded.

If a sample containing charged particles of different types is introduced at the earthed end of the stem portion 105, it will migrate along the stem portion under the influence of the voltage. The particles of different types migrate at different speeds, forming constituent bands 120. When each constituent band reaches the branch point, it can be switched into either of the side channels 110, 115 by applying the voltage to the selected side channel. In FIG. 1, it can be seen that some constituent bands 130 have previously reached the branch point and been switched into the right hand side channel 110 by applying the voltage according to CONDITION "R". However, the next constituent band 125 has reached the branch point and been switched into the left hand side channel 115 by applying the voltage according to CONDITION "L", thus separating it from the preceding bands 130.

Figure 2:
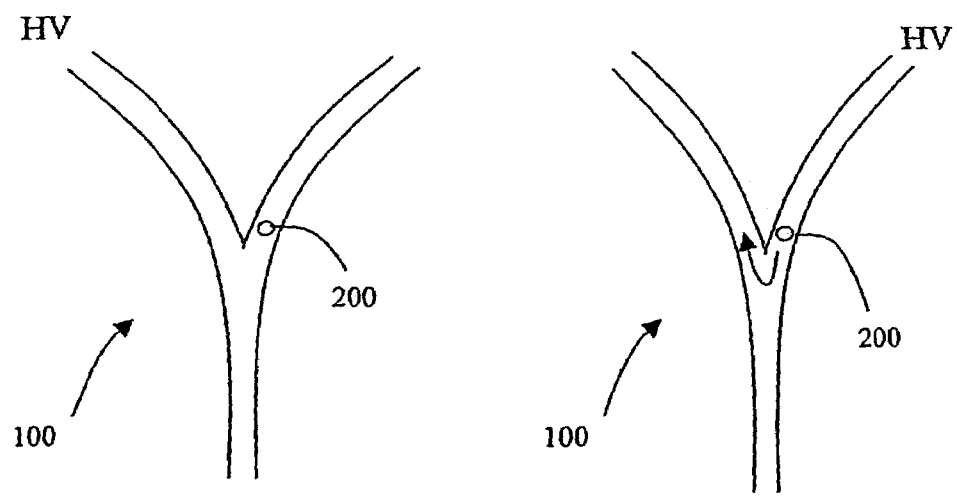
FIG. 2 demonstrates a problem which can occur with the branched microchannel of FIG. 1.

As mentioned above, problems can arise at the point of switching from the CONDITION "R" configuration to the CONDITION "L" configuration (or vice versa). It can be difficult to get clean separation of one constituent band from the next. Firstly for instance, it is possible that particles in the leading edge of a constituent band 120 still approaching the branch point start to travel up the wrong side channel. Secondly, it is possible that particles in the trailing edge of a constituent band 130 already travelling up a side channel come under the influence of the switched voltage and migrate back to the branch point and into the wrong side channel. FIG. 2 shows a charged particle 200 in such a trailing edge. If the voltage is switched from the CONDITION "R" configuration to the CONDITION "L" configuration, this particle and its near neighbours are still very close to the branch point and can change direction, migrating back to the branch point and into the left hand side channel 115, thus contaminating the constituent band 125 now being collected in the left hand side channel 115. The transport of the molecules from one side channel to another, as shown in FIG. 2, may be facilitated if the bifurcation point is slightly rounded (rather than being sharp as schematically illustrated in the drawing).

In embodiments of the present invention, contamination of this type can be reduced or avoided by applying a locally reversed voltage to any side channel not selected for collecting a constituent band. That is, a reversed voltage can be applied to a short portion of any non-selected channel which adjoins the branch point. Each time a different side channel is selected for collection of a constituent band, the reversed voltage is taken off the newly selected side channel and applied to a side channel which has been deselected. Alternatively, the reversed voltage may be applied temporarily, just during the period of switchover from one channel to another when there is the most significant risk of contamination occurring. The required period for this temporary switch condition can be pre-calculated according to the known or discovered mobilities and the needs of the case at hand: sometimes greater purity is desirable and a longer switch period can be applied.

The following is a description of a system for selecting the path of biological material flowing in an electrophoresis channel. This material may comprise for example nucleic acids such as deoxyribonucleic acid (DNA) and ribonucleic acid (RNA) or proteins in the form of peptides, protein digest fragments or any other form of proteinaceous material. Selection of any one or more particular fragment or band of material is accomplished primarily by using a branched microchannel 100 as shown in FIG. 1 and applying the voltage "HV" to the end of a selected side channel 115 for collection of the fragment or band 125 currently reaching the branch point between the two side channels 110,115. As soon as that fragment or band 125 is wholly collected in the selected side channel 115, the voltage "HV" is switched back to the end of the other side channel 110.

In order to reduce or avoid the contamination risk mentioned above, a reverse voltage drop is applied at the entrance to all non-selected branches. The reverse voltage drop can be applied at all times or just in the period immediately after a switch of the voltage "HV".

It should be noted that although only two side branches 110, 115 are shown in FIGS. 1 and 2, a switching system can be used so that flow can be directed down any one of a more complex configuration of channels. The reverse voltage is applied to every non-selected channel at a branch point so that molecules will migrate into only the selected side channel. Thus the principle can be extended to any branched structure by considering each branch point, which may have any number of branches coming from it, to be an instance of the singly branched structure. In another embodiment (not shown) there may be more than two channels at the or each bifurcation. By means of cascades and poly-furcations, very complex separating structures may be defined. Where required, previously-separated components may be selectively combined simply by merging together the resultant branch channels.

Figure 3:
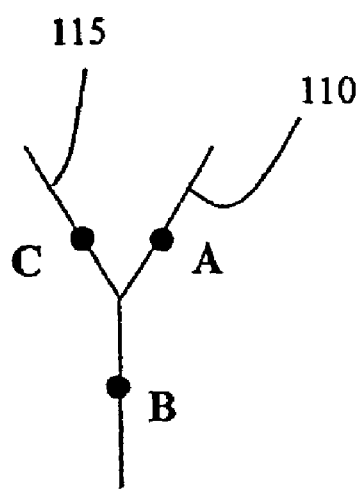
FIG. 3 shows schematically a set of connection points for use in applying a reverse voltage to the branched microchannel in order to avoid or ameliorate the problem of FIG. 2.

Referring to FIG. 3, the reverse voltage drop is applied between a point "B" just before the branch point and a point "A" or "C" just past the entrance of the branches down which no flow is desired. This causes the direction of molecular flow to be reversed in that region, which means that no molecules flowing toward the entrance to the side channel carrying the reverse voltage can enter, while any molecules which have progressed past the reversed section will continue to the end of the side branch that they are in.

To switch the molecules into the left hand side channel 115 as shown in FIG. 3, the voltages at the points "A", "B" and "C" bear the following relationship:

A<B<C

To switch the molecules into the right hand side channel 110 as shown in FIG. 3, the voltages at the points "A", "B" and "C" bear the following relationship:

C<B<A

The voltages can be applied in several different ways. One way is to use a fixed source of voltages and to switch these voltages, for instance between the points "A" and "C", to select different branches. An alternative is to use the intrinsic resistance of the channel and to connect points "A" or "C" directly to point "B".

Figure 4:
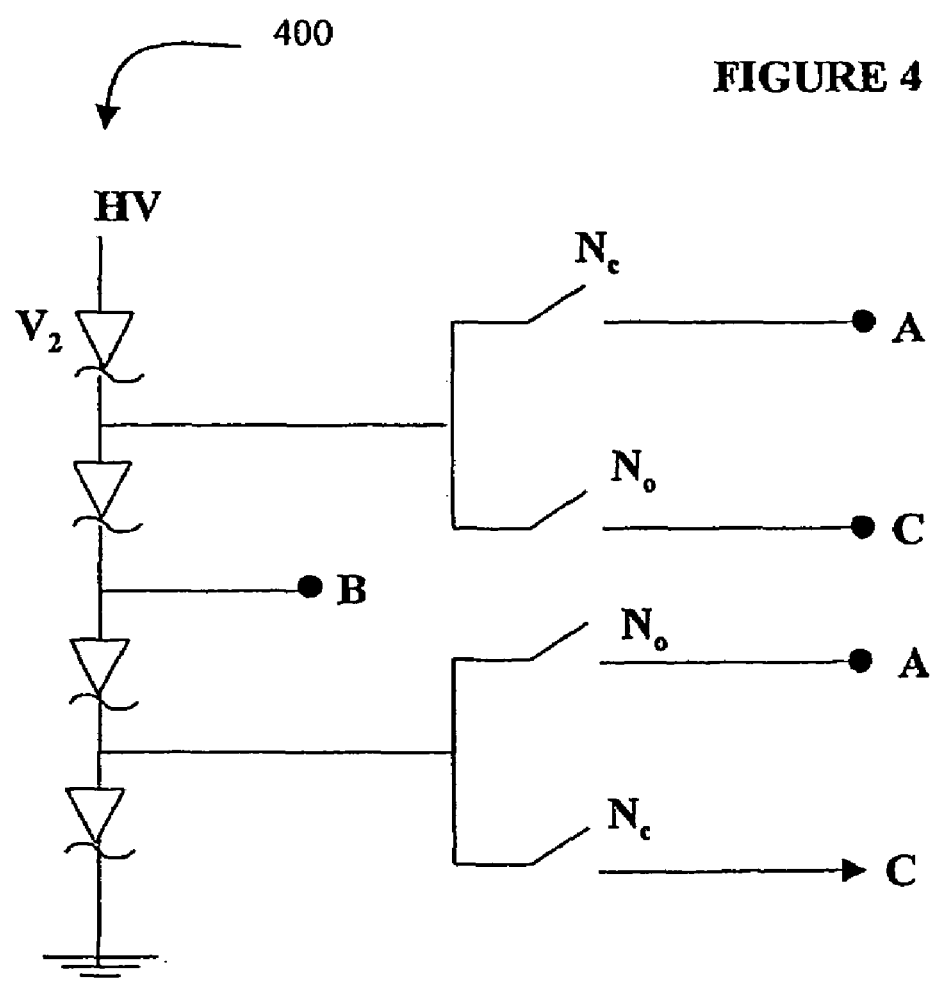
FIG. 4 shows schematically a Zener diode chain for use in the arrangement of FIG. 3.

Referring to FIG. 4, the voltages can be switched rapidly using a Zener diode chain 400. To switch the molecules into the right hand side channel 110 (CONDITION "R"), the $N_c$ switches are closed and to switch them into the left hand side channel 115 (CONDITION "L"), the $N_o$ switches are closed. Alternatively, it would be possible to use independently-operated voltage sources.

Figure 5:
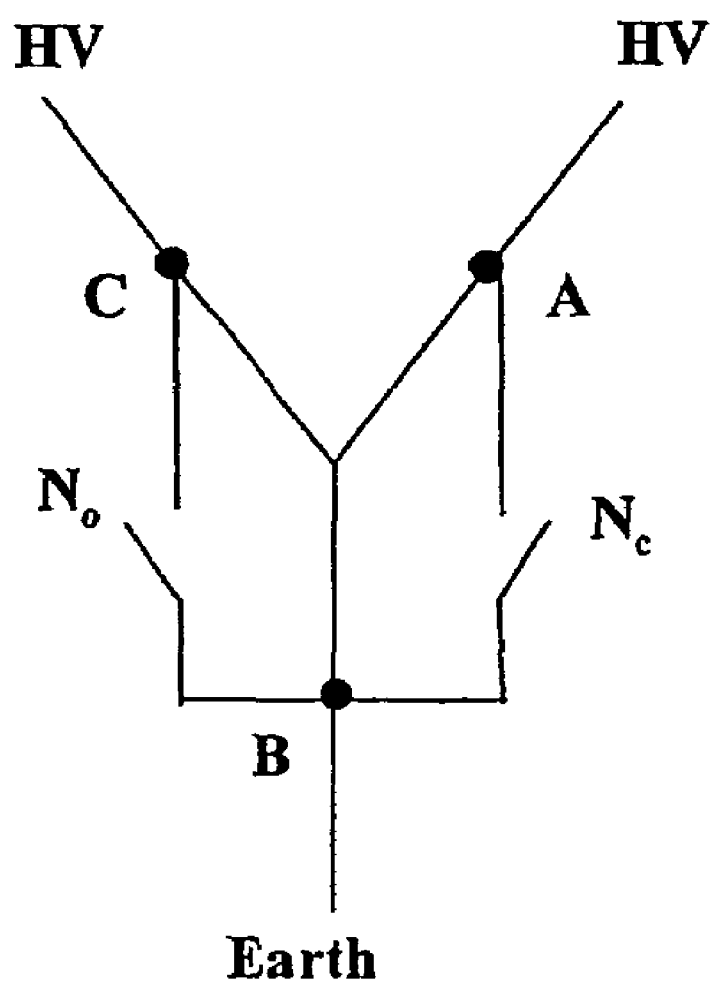
FIG. 5 shows an alternative arrangement for applying a reverse voltage using the connection points of FIG. 3.

Referring to FIG. 5, another approach is to supply the voltage HV to both of the side channels 110, 115 and to short the points "A" and "B", or "C" and "B", appropriately. This is convenient, since lower voltages can be used. The arrangement can be used with a constant current power supply, since the power drain is similar whichever side is chosen. That is of course not the case where a Zener diode chain 400 is used, such as that shown in FIG. 4.

Typically, where the branched microchannel has been fabricated on a chip, the physical distance between the points "A" and "B" may be of the order of a few millimetres. As mentioned above, an alternative arrangement is a bifurcated capillary in which case the spacing between points "A" and "B" may be of the order of a few centimetres. However, it is expected that these lengths may be very substantially reduced in future, as the technology develops.

The HV supply will normally be around +100 volts where the branched microchannel has been fabricated on a chip and up to +5000 volts for an embodiment using a bifurcated capillary.

The back-voltage applied between the points "A" and "B", or between "C" and "B", is of the order of tens of volts.

A similar approach to any of those described above can be used to deal with repeated bifurcations in the channels.

If a detector is placed underneath the chip or the capillary, the movement of the constituent bands can be tracked in real time. It would then be possible to switch the voltages automatically, by computer, for example based on pattern matching. So, if the computer noted that a particular sequence of bands was moving down towards the junction, it could selectively switch out certain bands into a side channel for further investigation while the rest of the sample continues to pass down another channel. An arrangement such as that shown in FIG. 5 lends itself particularly well to automated switching of this type since it is unnecessary to switch the higher "HV" voltage to achieve selection of a new side channel.

The invention is not limited to molecules flowing along channels by means of electrophoresis. In other embodiments, the molecules or other components to be separated may be urged along the channel by any suitable force, including although not limited to pressure, gravity, or centrifugal force.

It should be noted that the word "comprising" as used herein is intended to be broadly interpreted so as to include for instance at least the meaning of either of the following phrases: "consisting solely of" and "including amongst other things".

The invention claimed is:

1. A separating device for electrophoretically separating components flowing along an electrophoresis channel, the device comprising a main channel branched at a branch point connected to at least two subsidiary channels, a first voltage source, for connection to the main channel and at least one subsidiary channel to produce a potential along the main channel and at least one subsidiary channel in a first direction for electrophoretically separating the components, and switchable voltage control means for controlling a voltage in a region of the branch point to provide potential differences of opposing polarity along the subsidiary channels such that the components to be separated are caused to flow from the main channel into a selected subsidiary channel, wherein the voltage control means is arranged to control the voltage such that the potential difference along the selected subsidiary channel is in the first direction and the potential difference in the remaining subsidiary channel or channels is in a second, opposed direction.

2. A separating device according to claim 1 wherein the switchable voltage control means is adapted, on switching, to reverse the polarity of the potential differences along each of two subsidiary channels at a branch point so that any one subsidiary channel can be selected to be subject to a different polarity from every other subsidiary channel at that branch point.

3. A separating device according to claim 1 wherein the voltage control means operates in dependence upon the flow behaviour of the components to be separated.

4. A separating device according to claim 1 wherein the voltage control means is provided with a detector for use in controlling voltage, the detector being adapted to detect flow behaviour of at least one component to be separated.

5. A separating device according to claim 1, wherein the main channel is branched at more than one branch point and the voltage control means is adapted to control voltage in a region of each branch point independently.

6. A separating device according to claim 1, comprising a second voltage source for use by the voltage control means in a region of one or more branch points.

7. A separating device according to claim 1, wherein the first voltage source is operable to connect to all the subsidiary channels at the same time to produce a potential difference along the main channel and each subsidiary channel, and wherein the voltage control means comprises means for short circuiting a point along the main channel to a point along at least one of the subsidiary channels, in a region of the branch point for that subsidiary channel.

8. A separating device according to claim 1, wherein the voltage control means comprises a diode chain connected between the voltage source and earth, at least one subsidiary channel at a branch point being switchably connected to at least two alternative points in the diode chain so as to provide first and second configurations, the potential difference along the subsidiary channel in a region of the branch point in the first configuration having opposite polarity to the potential difference along the subsidiary channel in a region of the branch point in the second configuration.

9. A separating device according to claim 1 in which at least one of the subsidiary channels is further branched at a further branch point, the device including a further switchable voltage control means for controlling a further voltage in a region of the further branch point.

10. A method of separating an electrically charged component from a mixture, by differential flow along a branched channel structure, the method comprising the steps of:
    applying an electrophoretic potential to the mixture so as to electrophoretically move the mixture along a main channel of a channel structure to a branch point connecting the main channel to at least two branch channels; and
    applying an electrical potential difference to a portion of each branch channel in a region of the branch point, wherein the electrical potential difference applied to a selected branch channel presents the same polarity at the branch point as the electrophoretic potential and the polarity presented at the branch point by an electrical potential difference applied to another branch channel at the said branch point is opposed to the electrophoretic potential.

11. A method according to claim 10 further comprising the steps of reversing the polarity presented by the electrical potential difference applied to the selected branch channel, and reversing the polarity presented by the electrical potential difference applied to the said another branch channel at the branch point, so as to change the selected branch channel from a first to a second branch channel.

* * * * *